United States Patent [19]

Semeria et al.

[11] Patent Number: 5,648,544
[45] Date of Patent: Jul. 15, 1997

[54] PROCESS FOR THE PREPARATION OF 2-AMINOALKANE-1,3-DIOLS

[75] Inventors: Didier Semeria, Courtry; Michel Philippe, Wissous, both of France

[73] Assignee: L'Oreal, Paris, France

[21] Appl. No.: 564,739

[22] Filed: Nov. 29, 1995

[30] Foreign Application Priority Data

Nov. 30, 1994 [FR] France .................. 94 14380

[51] Int. Cl.$^6$ .................................. C07C 209/40
[52] U.S. Cl. .................. 564/468; 564/224; 564/258; 564/489
[58] Field of Search .................. 564/468, 489, 564/224, 258

[56] References Cited

U.S. PATENT DOCUMENTS

| 5,012,000 | 4/1991 | Illig et al. | 564/489 |
| 5,488,167 | 1/1996 | Hudlicky | 564/489 |

FOREIGN PATENT DOCUMENTS 0500437  8/1992  European Pat. Off. .

OTHER PUBLICATIONS

Gregory and Malkin, Jounal of the Chemical Society, 1951 pp. 2453–2456.
Hayes and Gever, Journal of Organic Chemistry, vol. 16, 1951 pp. 269–278.
Fisher, Chemistry and Industry, 1952 pp. 130–131.
Adkins and Billica, Journal of the American Chemical Society, vol. 71, 1948, pp. 3121–3125.

*Primary Examiner*—Brian M. Burn
*Attorney, Agent, or Firm*—Finnegan, Henderson, Farabow, Garrett & Dunner

[57] ABSTRACT

A process for the preparation of 2-aminoalkane-1,3-diols by a single step reduction of alkyl 2-oximino-3-oxoalkanoates. The reduction is carried out in the presence of at least one hydride, in a solvent, under inert atmosphere and at a controlled initial temperature.

Synthetic yields are markedly improved.

31 Claims, No Drawings

PROCESS FOR THE PREPARATION OF 2-AMINOALKANE-1,3-DIOLS

The invention relates to a novel process for the preparation of precursors for the synthesis of ceramides.

In the natural state, ceramides are the main component of the lipid layers of the epidermis. They are used in cosmetics in natural or synthetic form in composition intended, inter alia, to reduce drying of the skin or to impart better elasticity thereto, or alternatively compositions intended for treating the hair.

Natural ceramides are generally obtained by extraction from pigskin, cow's brain, eggs, blood cells or plants (JP 86/260008 or JP 87/120308).

The many drawbacks associated with this type of supply (fragility, contamination, storage, costs, etc.) are such that the chemical synthesis route was explored at a very early stage.

Much work has been developed on these synthetic routes (Hayes and Gever J. Org. Chem. 1951, 16, 269; Gregory and Malkin J. Chem. Soc., 1951, 2453–2456; Fisher, N., Chemistry and Industry 1952, 130–131; Shapiro, D. Chemistry of sphingolipids, Hermann, Paris, 1969, 26–34).

Hayes and Gever propose a direct synthesis route starting with a methyl 2-oximino-3-oxoalkanoate in a reduction step using lithium aluminium hydride. Hoover, this route leads only to the production of a mixture of long-chain amino compounds, from which no purified compound can be extracted. The yield for this reaction, whose poor extent (2%) is emphasized by the authors themselves, is such that this method cannot reasonably find industrial application.

In 1951, Gregory and Malkin approached the field of the synthesis of sphingolipids and precursors in the synthesis of ceramides, namely 2-aminoalkane-1,3-diols.

They teach of a multi-step synthetic route starting with a methyl 2-oximino-3-oxoalkanoate which, by successive reductions, results in the synthesis of 2-aminoalkane-1,3-diols. In this case also, on account of the large number of synthetic steps and purification steps of the intermediates, this route affords mediocre results as regards the yield. Furthermore, this succession of steps considerably prolongs the time required to prepare these compounds.

In 1952, Fisher mentioned the synthetic route recommended by Gregory & Malkin, pointing out, however, that after a protection reaction by benzoylation, without detailing the reactions used, he was able to obtain a tribenzoyl 2-aminoalkane-1,3-diol by direct reduction. Once debenzoylated, this compound could lead to a 2-aminoalkane-1,3-diol.

In 1969, Shapiro repeated these synthetic routes, improving the steps for protection of the sensitive functions, in particular the amine. This multi-step synthetic route is that which has since been used for the synthesis of ceramides and precursors thereof (FR 2,673,179).

As may readily be appreciated from the above text, the production of ceramide precursors, namely 2-aminoalkane-1,3-diols, although relatively well defined, requires several successive reactions. The effect of this is to make the synthesis of ceramides long and expensive.

This succession of reactions also has the effect of considerably reducing the yields, thereby contributing towards the increase in cost price of these compounds.

The Inventors have thus sought to Improve the routes for the synthesis of ceramides and in particular precursors thereof, 2-aminoalkane-1,3-diols, without the need to protect and then deprotect various functions.

After extensive research and in a Surprising and unexpected manner, contrary to what the prior art has been teaching constantly for several years, the inventors discovered that the direct synthesis route starting with an alkyl 2-oximino-3-oxoalkanoate may lead to a 2-aminoalkane-1,3-diol in a single reduction step.

By dispensing with several steps, the invention makes it possible to save a considerable amount of time and to enhance the yield for the synthesis very considerably, which reduces the industrial cost price of ceramides synthesized from the compound obtained by the process claimed.

Thus, the subject of the invention is a process for the preparation of 2-aminoalkane-1,3-diol, characterized by a one-step reduction of the reducible functions of an alkyl 2-oximino-3-oxoalkanoate of formula (I):

$$R_1—CO—CNOH—COOR_2 \quad (I)$$

in which $R_1$ and $R_2$ represent a saturated or unsaturated linear or branched alkyl radical, in the presence of at least one hydride, in a solvent, under inert atmosphere, and at a controlled initial temperature.

According to a preferred embodiment of the process, $R_1$ has from 5 to 29 carbon atoms and $R_2$ has from 1 to 5 carbon atoms. $R_1$ more preferably has from 11 to 21 carbon atoms.

According to a preferred mode of the invention, $R_2$ is a methyl or ethyl radical.

The process according to the invention allows the one-step synthesis of the 2-aminoalkane-1,3-diols corresponding to formula (II):

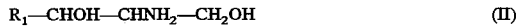

$$R_1—CHOH—CHNH_2—CH_2OH \quad (II)$$

or corresponding salts.

Preferably, the yield obtained by the process of the present invention in converting the compound of formula (I) to the compound of formula II or salt thereof is greater than 50%. More preferably, the yield is greater than 70%.

After synthesis, the compound of formula (II) is in the form of a D,L-erythro/threo mixture. This mixture Is generally in erythro/threo proportions ranging from 90/10 to 20/80 and is preferably from 85/15 to 35/65.

The reductive reaction is carried out in a solvent. This solvent is preferably anhydrous and inert towards the reactants present. Solvents which may be mentioned, for example, are toluene, heptane, tetrahydrofuran, tert-butyl methyl ether or isopropyl ether. tert-Butyl methyl ether is preferably used.

The reduction, i.e. the reductive reaction, is performed under inert atmosphere, in order to avoid destruction of the reactant by air or water. Nitrogen or argon is generally used to do this. The reductive reaction is preferably performed under an atmosphere composed of nitrogen.

The expression "controlled initial temperature" means that the reductive reaction is initiated at a temperature ranging from −10° C. to room temperature (about 20° C.). The reaction is preferably initiated at 0° C.

After initiation, the reaction may be carried out at any temperature, preferably from −10° C. to the reflux temperature of the solvent used. The reaction is preferably performed at the reflux temperature of the solvent used. In other words, after initiation, the temperature may be raised or lowered as desired.

Among the hydrides which may be used according to the invention, there may be mentioned lithium borohydride (LIBH$_4$), lithium aluminium hydride (LiAlH$_4$), aluminium hydride (AlH$_3$) or sodium bis(2-methoxyethoxy) dihydroaluminate (RedAl™ sold by the company Aldrich, or vitride sold by the company Hexcel). Sodium bis(2-methoxyethoxy)dihydroaluminate is preferably used.

At the end of the reductive reaction, the synthesized product may be in the form of aluminium complexes. It is preferable, in order to limit the formation of these complexes, that the minimum amounts of hybride are used.

Thus, the hydride is generally present in the reaction at a concentration ranging from 2 to 6 molar equivalents relative to the alkyl 2-oximino-3-oxoalkanoate. A concentration ranging from 2 to 4 molar equivalents relative to the alkyl 2-oximino-3-oxoalkanoate is preferably used.

At the end of the reductive reaction, marked by the disappearance of the starting materials, in order to destroy the complexes possibly formed, the pH of the reaction medium is preferably brought to a value below 2 or above 11, by addition of aqueous acid or base to the reaction medium.

The reaction medium is preferably brought to a pH ranging from 0.5 to 1.5 or from 11.5 to 12.5. Thus, hydrochloric acid or sodium hydroxide respectively is preferably used.

The alkyl 2-oximino-3-oxoalkanoates used in the reductive reactions according to the invention may be prepared according to the techniques commonly used, in particular by reacting an alkyl 3-oxoalkanoate with an alkyl nitrite in anhydrous medium acidified with gaseous hydrogen chloride. Preferably, an alkyl 3-oxoalkanoate is reacted with an alkyl nitrite in the presence of an acidic aqueous solution, in catalytic amount, for example, concentrated hydrochloric acid.

The term "catalytic amount" means from 0.05 to 0.8 molar equivalent of acid and preferably from 0.1 to 0.6 molar equivalent of acid.

The term "alkyl nitrite" means a compound having the formula $R_3ONO$, in which $R_3$ represents an alkyl radical having from 2 to 6 carbon atoms, for example butyl nitrite.

The compound obtained according to the invention may be used in ceramide synthesis processes such as those described by Shapiro, D, (Chemistry of sphingolipids, Hermann, Paris, 1969, 26–34).

Thus, for example, it is possible to prepare the desired ceramide by acylation of the amine function of a 2-aminoalkane-1,3-diol with an acid chloride, with an anhydride, with a para-nitrophenyl ester, with a succinimide ester, with a dicyclohexylcarbodiimide ester, with a lower alkyl ester or with an azolide such as, in particular, an imidazolide or a pyrazolide, in an anhydrous medium or in a solvent such as tetrahydrofuran, pyridine, dimethylformamide or dichloromethane. Preferably, the anhydride is a mixed anhydride, the lower alkyl ester is a methyl or ethyl ester and the azolide is an imidazolide or a pyrazolide.

An example of synthesis according to the invention will now be given without any limitation to the invention:

EXAMPLE 1

Synthesis of 2-aminooctadecane-1,3-diol 1 mol of methyl 3-oxooctadecanoate was dissolved in ethyl acetate. 1.05 mols of butyl nitrite were added to this solution, followed by slow addition, at room temperature, of 33 grams of concentrated hydrochloric acid until the starting material completely disappeared.

The reaction mixture was then washed with water, followed by evaporation of the organic phase; the residual oil was redissolved in heptane and then recrystallized under cold conditions, filtered, washed and dried. Methyl 2-oximino-3-oxooctadecanoate was thus obtained in a yield of 80%. The analysis of this product showed it to be in accordance with the expected structure.

4 mols of RedAl™ solution (70% by weight in toluene) were mixed into tert-butyl methyl ether, under nitrogen. The solution was then cooled to a temperature of 0° C. and 1 mol of methyl 2-oximino-3-oxooctadecanoate was added slowly. The reaction medium was then heated gradually to 50° C. After the reaction, marked by the disappearance of the starting materials, the reaction medium was hydrolysed under cold conditions using sodium hydroxide solution. The aqueous phase was separated out after settling of the phases had taken place and the organic phase was rewashed with water, then dried.

After cooling the organic phase, the precipitate was filtered off and dried. 2-Aminooctadecane-1,3-diol was obtained in the form of a white powder, in a yield of 80%.

Analysis: m.p.: 81° C. $^{13}C$ NMR: in agreement with the structure: % Erythro/Threo: 54/46 Elemental Analysis: correct.

We claim:

1. A process comprising the step of:
   reducing, in a single step, an alkyl 2-oximino-3-oxoalkanoate of the formula (I):

$$R_1\text{—CO—CNOH—COOR}_2 \qquad (I)$$

in which $R_1$ and $R_2$ represent a saturated or unsaturated linear or branched alkyl radical,
   in the presence of at least one hydride, in a solvent, under inert atmosphere, and at a controlled initial temperature for a time sufficient to obtain a 2-aminoalkane-1,3-diol of the formula (II):

$$R_1\text{—CHOH—CHNH}_2\text{—CH}_2\text{OH} \qquad (II)$$
   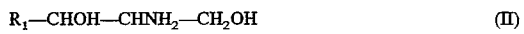

or a salt of the 2-aminoalkane-1,3-diol of the formula (II).

2. A process according to claim 1, in which $R_1$ represents an alkyl radical having from 5 to 29 carbon atoms.

3. A process according to claim 2, in which $R_1$ represents an alkyl radical having from 11 to 21 carbon atoms.

4. A process according to claim 1, in which $R_2$ represents an alkyl radical having from 1 to 5 carbon atoms.

5. A process according to claim 4, in which $R_2$ represents a methyl or ethyl radical.

6. A process according to claim 1, in which the compound of formula (II) or salt thereof is in the form of a D,L-erythro/threo mixture in proportions of erythro to threo ranging from 90/10 to 20/80.

7. A process according to claim 6, in which the proportions of erythro to threo range from 85/15 to 35/65.

8. A process according to claim 1, in which the solvent is a solvent which is inert with respect to the compound of formula (I) and the hydride.

9. A process according to claim 1, in which the solvent is an anhydrous solvent.

10. A process according claim 1, in which the solvent is toluene, heptane, tetrahydrofuran, tert-butyl methyl ether or isopropyl ether.

11. A process according to claim 1, in which the inert atmosphere is nitrogen or argon.

12. A process according to claim 11, in which the inert atmosphere is nitrogen.

13. A process according to claim 1, in which the at least one hydride is lithium borohydride ($LiBH_4$), lithium aluminium hydride ($LiAlH_4$), aluminium hydride (AlH), or sodium bis(2-methoxyethoxy)dihydroaluminate.

14. A process according to claim 13, in which the hydride is sodium bis(2-methoxyethoxy)dihydroaluminate.

15. A process according to claim 1, in which the at least one hydride is at a concentration ranging from 2 to 6 molar equivalents relative to the alkyl 2-oximino-3-oxoalkanoate.

16. A process according to claim 15, in which the at least one hydride is at a concentration ranging from 2 to 4 molar equivalents relative to the alkyl 2-oximino-3-oxoalkanoate.

17. A process according to claim 1, in which the reducing step is begun at a controlled initial temperature, and ends at any temperature ranging from −10° C. to the reflux temperature of the solvent.

18. A process according to claim 17, in which the reducing step ends at the reflux temperature of the solvent.

19. A process according to claim 1, in which the reducing step is initiated at a temperature of 0° C.

20. A process according to claim 1, in which, at the end of the reducing step, the reducing step medium is brought to a pH below 2.

21. A process according to claim 1, in which, at the end of the reducing step, the reducing step medium is brought to a pH above 11.

22. A process according to claim 20 in which the reducing step medium is brought to a pH ranging from 0.5 to 1.5.

23. A process according to claim 21 in which the reducing step medium is brought to a pH ranging from 11.5 to 12.5.

24. A process according to claim 20 in which hydrochloric acid is used to bring the pH below 2.

25. A process according to claim 21 in which sodium hydroxide is used to bring the pH above 11.

26. A process according to claim 1, further comprising the step of, prior to said reducing step, reacting an alkyl 3-oxoalkanoate with an alkyl nitrite, in anhydrous medium, acidified with gaseous hydrogen chloride, to obtain the alkyl 2-oximino-3-oxoalkanoate of formula (I).

27. A process according to claim 1, further comprising the step of, prior to said reducing step, reacting an alkyl 3-oxoalkanoate with an alkyl nitrite in the presence of a catalytic amount of concentrated hydrochloric acid aqueous solution, to obtain the alkyl 2-oximino-3-oxoalkanoate of formula (I).

28. A process according to claim 1, further comprising the step of, after said reducing step, acylating, in an anhydrous medium or in a solvent, the amine function of the 2-aminoalkane-1,3-diol of formula (II) or a salt thereof with an acylating agent, said agent being an acid chloride, an anhydride, a para-nitrophenyl ester, a succinimide ester, a dicyclohexylcarbodiimide ester, a lower alkyl ester or an azolide, for a time sufficient to obtain a ceramide.

29. A process according to claim 28 in which said azolide is an imidazolide or a pyrazolide.

30. A process according to claim 28 in which said solvent in said step after said reducing step is tetrahydrofuran, pyridine, dimethylformamide or dichloromethane.

31. A process according to claim 28 in which said anhydride is a mixed anhydride and said lower alkyl ester is a methyl or ethyl ester.

* * * * *